United States Patent [19]
Berger et al.

[11] Patent Number: 5,206,353
[45] Date of Patent: Apr. 27, 1993

[54] CD-4/CYTOTOXIC GENE FUSIONS

[75] Inventors: Edward A. Berger, Rockville; Bernard Moss, Bethesda; Thomas R. Fuerst, Gaithersburg; Ira Pastan, Potomac; David Fitzgerald, Silver Spring; Tamio Mizukami, Bethesda; Vijay K. Chaudhary, Rockville, all of Md.

[73] Assignee: The United States of America as represented by the Department of Health and Human Services, Washington, D.C.

[21] Appl. No.: 223,270

[22] Filed: Jul. 22, 1988

[51] Int. Cl.$^5$ .............................................. C12N 15/11
[52] U.S. Cl. .................................. 536/23.4; 435/69.7; 435/172.3; 435/320.1; 435/252.33
[58] Field of Search .......... 536/27; 435/172.3, 252.33, 435/320.1; 935/9, 29

[56] References Cited
PUBLICATIONS

Chaudhary, et al. *Proc. Natl. Acad. Sci. USA* 84:4538–4542, 1987.
McDougal, et al. *Science* 231:382–385, 1986.
Maddon, et al. *Cell* 42: 93–104, 1985.
Chakrabaty et al. *Nature* 320:535–537, 1986.

*Primary Examiner*—Richard A. Schwartz
*Assistant Examiner*—J. LeGuyader
*Attorney, Agent, or Firm*—NIH/Office of Technology Transfer

[57] ABSTRACT

A chimeric gene directing the synthesis of hybrid recombinant fusion protein in a suitable expression vector has been constructed. The fusion protein possesses the property of selective cytotoxicity against specific virus-infected cells. A CD4(178)-PE40 hybrid fusion protein has been made for selectively killing HIV-infected cells.

9 Claims, 6 Drawing Sheets

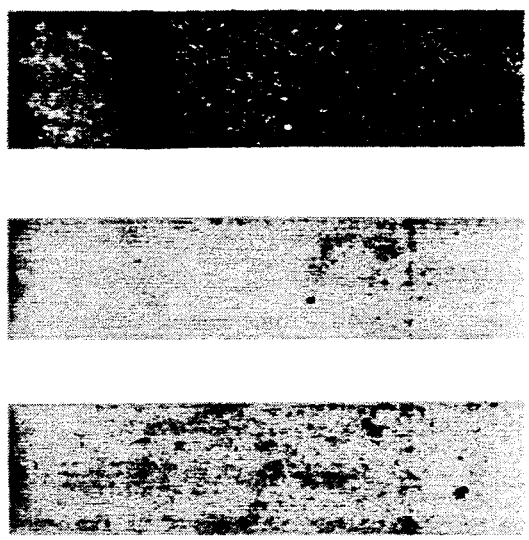

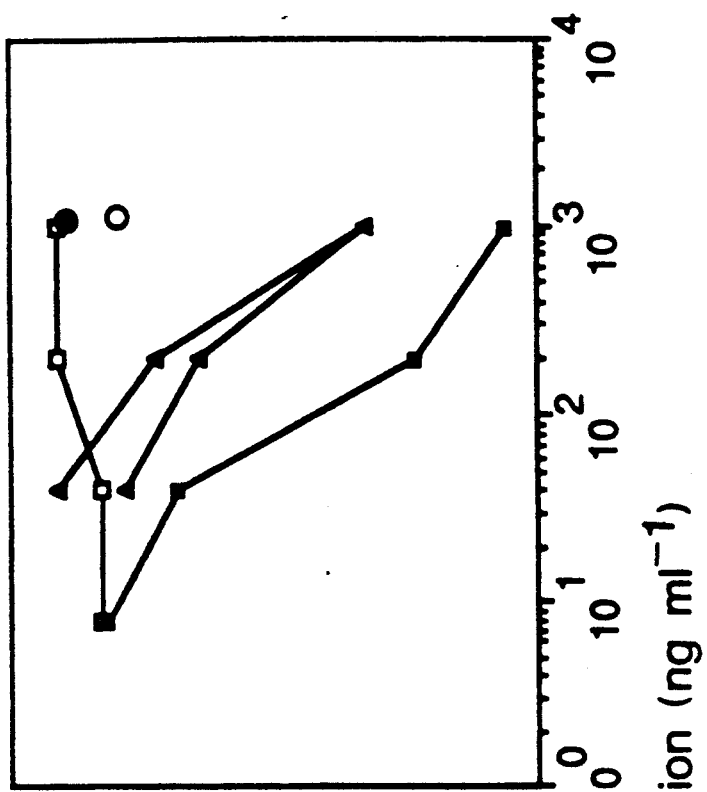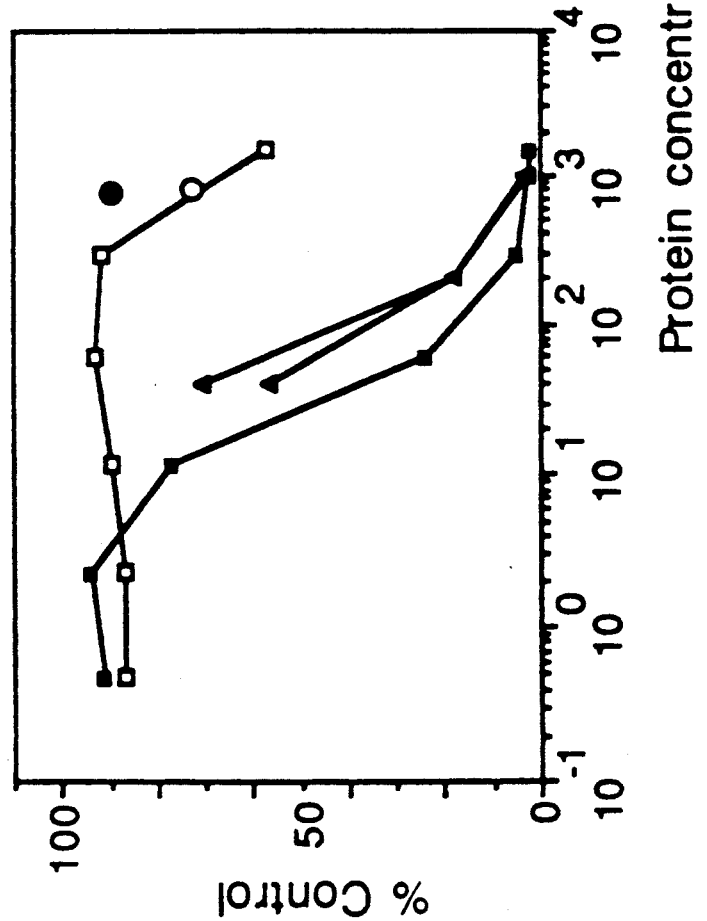

CD-4/CYTOTOXIC GENE FUSIONS

TECHNICAL FIELD

The present invention is related generally to the control of viral infection. More particularly, the present invention is related to the construction of a chimeric gene expressing a recombinant fusion protein which selectively kills specific virus-infected cells. A hybrid fusion protein having selective cytotoxicity against HIV infected cells has been made.

BACKGROUND OF INVENTION

It is estimated that in the absence of effective therapy, most, if not all, individuals infected with human immunodeficiency virus (HIV) will develop acquired immune deficiency syndrome (AIDS) and ultimately succumb to a combination of opportunistic microbial infections and malignancies. It is further estimated that without an effective vaccine, the number of infected individuals is likely to increase substantially.

Anti-viral agents, immunomodulators and inhibitors of specific HIV functions are being tested as potential treatments to alleviate the high morbidity and mortality related to AIDS. However, a potent cytotoxic agent targeted to selectively kill HIV-infected cells has not heretofore been developed.

SUMMARY OF INVENTION

It is therefore, an object of the present invention to provide a chimeric gene which directs the synthesis, in a suitable expression vector, of a hybrid protein comprising a virus binding region from a cellular receptor sequence linked to a protein toxin sequence containing a region essential for cell toxicity.

It is a further object of the present invention to provide an isolated, substantially pure fashion protein comprising the HIV binding portion of the human CD4 molecule and active regions of Pseudomonas exotoxin A.

It is another object of the present invention to provide a method of controlling AIDS virus infection, comprising contacting HIV-infected cells with effective amounts of the fusion protein of the present invention to selectively kill the HIV-infected cells.

Other objects and advantages of the present invention will become evident from the following detailed description of the invention.

BRIEF DESCRIPTION OF THE DRAWINGS

These and other objects, features and many of the attendant advantages of the invention will be better understood upon a reading of the following detailed description when considered in connection with the accompanying drawings wherein:

FIG. 4 shows the selective cytotoxic effect of CD4(178)-PE40 on cells expressing HIV-1 envelope glycoprotein: A. cells expressing the HIV-1 envelope glycoprotein encoded by a recombinant vaccinia virus. Closed symbols represent cells infected with vPE-16, a vaccinia recombinant containing the HIV-1 gp160 gene linked to the vaccinia 7.5 K promoter, inserted within the thymidine kinase locus. Open symbols represent cells infected with a control vaccinia recombinant, vTF7-3, which contains the bacteriophage T7 RNA polymerase gene also linked to the vaccinia 7.5 k promoter and inserted within the thymidine kinase locus. The toxin preparations used were: $\triangle$, $\blacktriangle$ PE, O, $\bullet$ PE40, $\square$, $\blacksquare$ CD4(178)-PE40. B. Cells chronically infected with HIV-1. Closed symbols represent the 8E5 human T-cell line which contains a single integrated copy of the HIV-1 (LAV) genome. The virions produced are non-infectious due to a premature chain termination mutation in the reverse transcriptase gene. Open symbols represent the parental non-infected A3.01 cell line. The toxin preparations used were: $\triangle$, $\blacktriangle$ PE, O, $\bullet$ PE40, $\square$, $\blacksquare$ CD4(178-PE40).

DETAILED DESCRIPTION OF THE INVENTION

Figure 1:
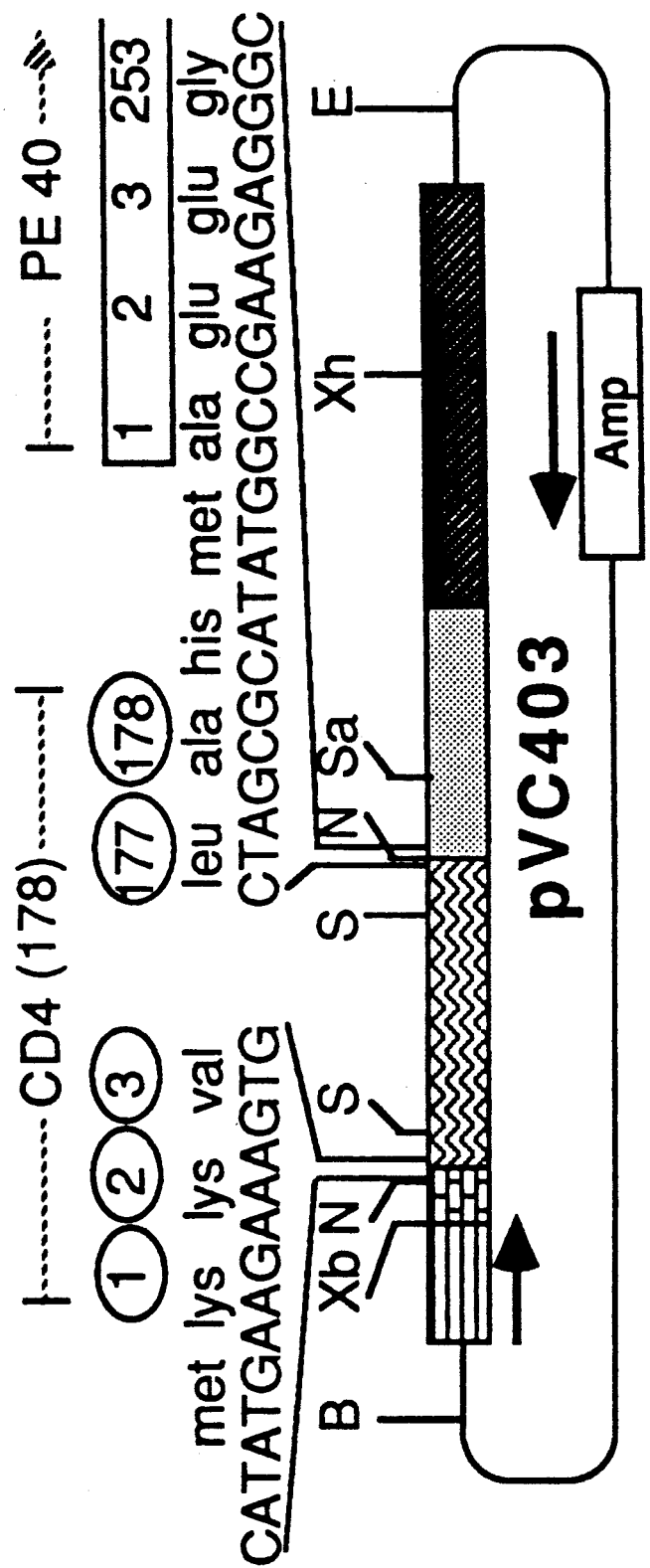
FIG. 1 is a schematic representation of the plasmid used for expressing CD4(178)-PE40.

The above and various other objects and advantages of the present invention are achieved by a chimeric gene which encodes a recombinant fusion protein having selective toxicity against specific virus-infected cells. The principal aspect of the present invention is that a toxin, or a cytotoxic part thereof, could be genetically attached to a receptor protein (or a fragement thereof) so that the fusion product binds to cells infected with a virus, since all viruses depend on a cellular receptor for entry. CD4 is one such receptor required by HIVs of different types. Hence, this invention is demonstrated by a partial but essential CD4 linked fusion cytotoxic product. The same principle can be applied for other viruses.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed herein are standard methodologies well known to one of ordinary skill in the art.

The term "substantially pure" as used herein means a product which is at least 80% pure monomeric hybrid protein.

The term "selective" as used herein means that the fusion protein of the present invention preferentially attacks cells such as HIV-infected cells without significantly affecting the activity of other cells.

MATERIALS AND METHODS

Construction of Expression Vector for CD4(178)-PE40

The plasmid pVC403 was constructed as described below. pVC403 carries a fusion gene encoding the first 178 amino acids of mature CD4 [referred to as CD4(178)] based on amino acid sequence data and amino acids 1-3 and 253-613 of PE (referred to as PE40). The fusion gene is under control of a T7 late promoter. E. coli strain BL21 ($\lambda$DE3) carrying pVC403 was used to express the fusion protein upon IPTG induction. The direction of transcription from the T7 promoter and for the B-lactamase gene is shown by solid arrows in FIG. 1. The circled numbers are the amino acids of CD4 and the boxed numbers are the amino acids of PE. The boundaries of the CD4(178) sequence and the start of PE40 sequence are shown at the top.

Construction of pVC403

Plasmid pVC4 which carries a full length PE gene attached to a T7 promoter was cut with NdeI and Asp718 and ligated to a 52 bp linker containing codons for the first 16 amino acids of mature CD4 and NdeI and Asp718 cohesive ends. This intermediate plasmid (pVC401) has 3 RsaI sites, one between the first 16 codons of mature CD4 and the remainder of PE gene. pVC401 was partially cut with RsaI, then with XhoI, and a 2.8 Kb fragment was isolated. Plasmid pCD4SPE40TM1 which carries a fusion gene between the first 178 amino acids of CD4 [CD4(178)] and PE40 under a T7 promoter was restricted with RsaI and XhoI, and a 1.3 Kb fragment was isolated. Construction of pCD4SPE40TM1 is described below. The 1.3 Kb fragment from pCD4SPE40TM1 was ligated to a 2.8 Kb fragment from pVC401 to produce plasmid pVC403. This plasmid has a Nde I site at the junction of the CD4(178) and PE40 genes that can be used to introduce various other PE genes.

Construction of pCD4SPE40TM1

A 0.70-kb EcoRI-SalI fragment containing the amino-terminal two immunoglobulin-like domains of CD4 was excised from pCD4f and cloned into M13mp18. The resulting recombinat phage, mp18CD4TM1 was propagated in a dut⁻ung⁻ strain and the single-stranded template DNA was annealed with a 33 mer oligonucleotide, TM21 containing an NdeI site (CATATG) encoding histidine and methionine residues just after a codon encoding an alanine residue, the 178th amino acid of CD4. After second strand synthesis, the double-stranded DNA was transformed into a wild type strain, and a mutant clone mp18CD4TM21 was selected by NdeI digestion. To obtain a final expression plasmid for a fusion protein more easily, an intermediate plasmid, pCD4PE40TM1 was constructed as follows. A 1.23-kb fragment containing PE40 was excised from pVC8 by digesting it with EcoRI, filling in the cohesive end with DNA polymerase I Klenow fragment, and digesting it with XbaI. The fragment was ligated with a 5.21-kb fragment of pCD4TM1 (an expression plasmid for 372 amino-acid CD4); the fragment was obtained by digesting the plasmid with SalI, filling in the cohesive end with DNA polymerase I Klenow fragment, and digesting with NheI, yielding pCD4PE40TM1. From this plasmid, a 5.72-kb NdeI (partial)-EcoRI fragment was excised and ligated with a 0.69-kb NdeI-EcoRI fragment of mp18CD4TM21, yielding pCD4SPE40TM1. This plasmid is capable of expressing a 546 amino-acid fusion protein consisting of the first 178 amino acids of CD4 at the amino terminus, followed by histidine and methionine residues derived from the NdeI site used for joining the two molecules, followed by the carboxy terminal PE40 sequence.

A deposit of the plasmid pVC 403 has been made at the ATCC, Rockville, Md. on Jun. 23, 1988 under the accession number 67739. The deposit shall be viably maintained, replacing if it becomes non-viable, for a period of 30 years from the date of the deposit, or for 5 years from the last date of request for a sample of the deposit, whichever is longer, and made available to the public without restriction in accordance with the provisions of the law. The Commissioner of Patents and Trademarks, upon request, shall have access to the deposit.

Purification and Characterization of CD4(178)-PE40

BL21 (λDE3) carrying plasmid pVC403 was grown in LB medium at 37° C with ampicillin (100 ug/ml), induced at $OD_{650nm}$ 0.6 with 1 mM isopropyl βD-thiogalactoside (IPTG) and the incubation continued for 90 minutes at 37° C. The cells were fractionated into periplasm and spheroplasts. The spheroplasts were suspended in TE (50 mM Tris pH 8.0, 1 mM EDTA), sonicated three times at 100 watts for 30 seconds each and spun at $100,000 \times g$ for 60 minutes to isolate the supernatant (cytoplasm) and pellet (containing inclusion bodies). For localization experiments, the pellet was suspended in TE and the various fractions were analyzed by ADP-ribosylation assays and by SDS-PAGE, using Coomassie Blue staining and immunoblotting with rabbit antibodies to PE.

For partial purification of CD4(178)-PE40, a denaturation/renaturation procedure was employed. A 500 ml culture of BL21 (λDE3) containing pVC403 was induced and the inclusion body pellet fraction prepared as described above. The pellet was suspended in 6.5 ml extraction buffer (guanidine HCl 7M, Tris HCl 0.1M pH 8.0, EDTA 1 mM and DTT 1 mM) and sonicated for 20 seconds three times. The suspension was stirred for 1 hour in the cold and centrifuged at $100,000 \times g$ for 15 minutes, and the supernatant saved. The supernatant (6.5 ml) was added dropwise to 500 ml cold phosphate buffered saline with rapid stirring. After 48 hours, a portion was purified as follows: 110 ml was dialyzed against Buffer A (Tris HCl 20 mM pH 7.7) for 8 hours with two one liter changes, filtered through a 0.45 μm filter and applied on a Mono Q column (HR 5/5) at a flow rate of 1 ml/min. The column was washed with 5 ml buffer A and then developed with a 25 ml linear gradient (0–0.5 M NaCl) and finally with 5 ml 1 M NaCl in Buffer A. 1 ml fractions were collected and analyzed for total protein, ADP-ribosylation activity and reactivity by ELISA using immobilized anti-PE antibodies and anti-CD4 monoclonal antibodies OKT4A (Ortho) and BL41 (Pel-freeze). Protein concentration was determined using Bradford reagent with bovine serum albumin as a standard. ADP-ribosylation activity is expressed as units/ml; 1 unit is equal to the activity of 1 μg of PE40 determined under the same assay conditions. For SDS-PAGE, samples were boiled with Laemmli sample buffer and electrophoresed on 10–15% gradient gels (PhastGels, Pharmacia). Analysis of the purification is shown in FIG. 2:

(a) Mono Q column Chromatography of renatured soluble CD4(178)-PE40

110 ml of renatured material (6 mg protein) was applied to a Mono Q column; proteins were eluted with a NaCl gradient and fractions of 1 ml were collected.

(b) SDS-PAGE of samples at various stages of purification

Gels were either stained with Comassie blue (lanes 1–3), or immunoblotted with polyclonal antibodies to PE (lanes 4–6). Lanes 1 and 4, spheroplasts; lanes 2 and 5, fraction 19 from Mono Q column; lanes 3 and 6, authentic PE, 100 ng. Molecular weight of protein standards are shown in Kd. The molecular weight of authentic PE is 66 Kd.

Demonstration of Binding of CD4(178)-PE40 to HIV Envelope Protein gp120

Figure 3B:
FIG. 3 (parts a and b) demonstrates the binding of CD4(178)-PE40 to HIV envelope protein gp120 by (a) coprecipitation technique and (b) by immunofluorescence microscopy.
Figure 3D:
Figure 3C:
Figure 3E:
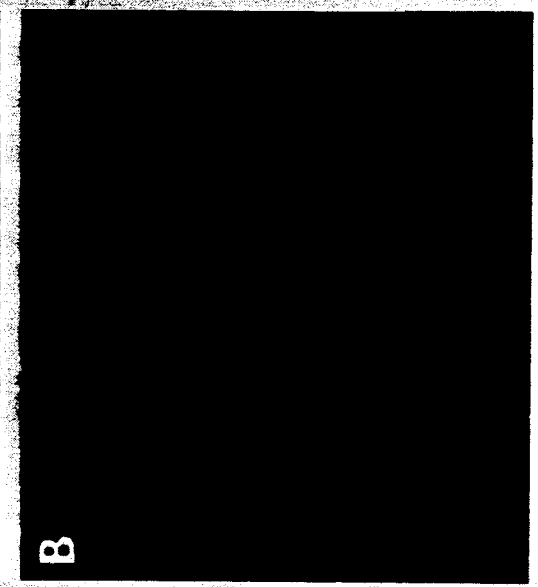

Two methods were employed to demonstrate this specific binding interaction. The first involved coprecipitation of radiolabeled gp120 along with CD4(178)-PE40 plus antibodies to PE. Media containing [$^{35}$S]-methionine-labeled gp120 was obtained as previously described using a vaccinia/bacteriophage T7 hybrid expression system. CV-1 cells were co-infected with two vaccinia virus recombinants: vPE6, encoding a secreted form of gp120 (HIV-1, IIB isolate) under control of the bacteriophage T7 promoter, and vTF7-3, encoding the T7 RNA polymerase driven by the vaccinia virus 7.5 K promoter. Five µl of media containing $^{35}$S-labeled gp120 was preincubated with 90 µl of crude renatured CD4(178)-PE40 for 4 hr at 4° C. Anti-PE antiserum (2 µl) was added, and after overnight incubation at 4° the immune complexes were precipitated with 10 µl Protein A-agarose (Calbiochem). The washed immunoprecipitates were analyzed by SDS-PAGE on 10% gels and the protein bands visualized by fluorography. The analysis is shown in FIG. 3a. The immune complex precipitated from a mixture of media containing [$^{35}$S]-labeled gp120 is shown in lane 3. For controls, either the anti-PE (lane 1) or the CD4(178)-PE40 (lane 2) were omitted.

The second method involved immunofluorescence. Confluent monolayers of CV-1 cells in 35 mm wells of 6-well plates (Costar) were infected with a recombinant vaccinia virus encoding gp160 (HIV-1, IIIB isolate) under control of the vaccinia 7.5K promoter. The multiplicity of infection was 1.5. As a control, cells were infected with vTF7-3 (see above). Ten hours post-infection, CD4(178)-PE40 (fraction 19 of the mono Q column, see FIG. 2) was added to a final toxin concentration of 50 µg/ml in PBS plus 0.2% (w/v) bovine serum albumin. After 1 hr at 4° C., the dishes were rinsed and incubated with a polyclonal anti-PE antiserum [1:500 in PBS plus 0.2% (w/v) bovine serum albumin] for an additional hour at 4° C. The cells were then incubated with affinity purified goat anti-rabbit IgG conjugated to rhodamine. Cells were fixed in formaldehyde, mounted and photographed. In the analysis shown in FIG. 3b, cells were infected with either the recombinant vaccinia virus containing the HIV-1 gp160 gene (A and A') or with the control vaccinia recombinant (B and B'). A and B are fluorescence micrographs and A' and B' are the corresponding phase contrast micrographs. Bar indicates 20 µm at 350×.

Demonstration of Selective Cytotoxicity for Cells Expressing the HIV Envelope Glycoprotein Two test systems were employed. The first involved cells expressing the HIV envelope glycoprotein encoded by a recombinant vaccinia virus. Duplicate assays were performed in 16 mm wells of 24-well plates (Costar). CV-1 cells were grown to 90% confluence (2×10$^5$ cells per well). The indicated recombinant vaccinia viruses were added to the wells at a multiplicity of infection of 20 in 0.25 ml of Dulbecco's MEM supplemented with 2.5% fetal bovine serum. After 90 min with occasional rocking, the medium was removed and replaced with 1 ml of the same medium containing 10% of the normal methionine concentration. 7.5 hr later, 0.05 ml of the indicated toxin preparations in Dulbecco's phosphate buffered saline were added to give the final concentrations shown. The incubations were continued for 4 hr, at which time 20 µCi of $^{35}$S-methionine was added to each well in 0.05 ml of methionine-free medium. After one hr the labeling medium was removed and the wells were rinsed twice with 1 ml of Dulbecco's phosphate buffered saline. Cells were harvested in 0.5 ml of 0.1 N NaOH containing 0.1% (w/v) bovine serum albumin and the protein was precipitated with trichloroacetic acid and radioactivity determined by scintillation counting. Results are expressed as % control incorporation (no toxin added). In the analysis shown in FIG. 4a, closed symbols represent cells infected with a vaccinia recombinant encoding gp160, whereas open symbols represent cells infected with a control vaccinia recombinant, vTF7-3, encoding the bacteriophage T7 RNA polymerase (see description of FIG. 3). The toxin preparations used were (Δ, ▲) PE, (O, ●) PE40, (□, ■) CD4(178)-PE40.

The second test system employed cells chronically infected with HIV. 8E5 is a human T-cell line which contains a single integrated copy of the HIV-1 (LAV) genome. The virions produced are non-infectious due to a premature chain termination mutation in the reverse transcriptase gene. As a control, the parental non-infected A3.01 cell line was used. Assays were performed in duplicate in 24-well plates. Individual wells were seeded with 7×10$^5$ cells of the indicated cell line in 0.9 ml of medium containing 1 part RPMI supplemented with 10% fetal bovine serum plus 8 parts of the same medium lacking methionine. The designated toxin preparations were added in 0.02 ml Dulbecco's PBS to give 111% of the final concentration shown. After 17.5 hr, 10 µCi of $^{35}$S-methionine in 0.1 ml of complete medium was added to each well, and the incubations continued for 1 hr. Contents of the wells were then quantitatively transferred to centrifuge tubes and spun for 10 min at 2800 RPM in a Beckman centrifuge. The supernatants were removed and the pellets suspended in 0.1% (w/v) SDS. Fifty µl aliquots were analyzed by trichloroacetic acid precipitation using Whatman GF/C filters. Results are expressed as % control incorporation (no toxin added). A background value was obtained by treating cells with 5 µg PE for 18.5 hr, then incubating with $^{35}$S-methionine for only 1 min. This value, which represented only 3% of the control incorporation, was subtracted in the calculations to yield the data shown in FIG. 4. Closed symbols represent the 8E5 cells, whereas open symbols represent the A3.01 cells. The toxin preparations used were: (Δ, ▲) PE, (O, ●) PE40, (□, ■) CD4(178)-PE40.

RESULTS

As shown in FIG. 1, a chimeric gene encoding the first 178 amino acids of CD4 and amino acids 1 to 3 and 253 to 613 of PE was constructed (FIG. 1). This segment of PE (designated PE40) lacks domain I but retains domains II and III which are responsible for translocation and ADP-ribosylation, respectively. The plasmid, pVC403, also contained a bacteriophage T7 late promoter and the Shine-Delgarno ribosome binding sequence for high expression in Escherichia coli BL21 (λDE3). The chimeric protein, designated CD4(178)-PE40, was synthesized in large amounts, remained intracellular and appeared to be primarily associated with inclusion bodies in the 100,000xg pellet of sonicated spheroplasts. The denatured protein had the expected Mr of approximately 60,000 and reacted with polyclonal antibodies to PE by immunoblot analysis (see below).

A purification scheme involving denaturation of the insoluble protein with guanidine followed by rapid dilution was used. An ELISA demonstrated that the renatured form of CD4(178)-PE40 reacted with polyclonal antibody to native PE and monoclonal antibodies OKT4A and BL4 directed to CD4. Enzymatic activity of the hybrid protein was shown by an affinity capture procedure; up to 30% of the ADP-ribosylation activity could be selectively immunoprecipitated by OKT4A monoclonal antibody.

Figure 2A:
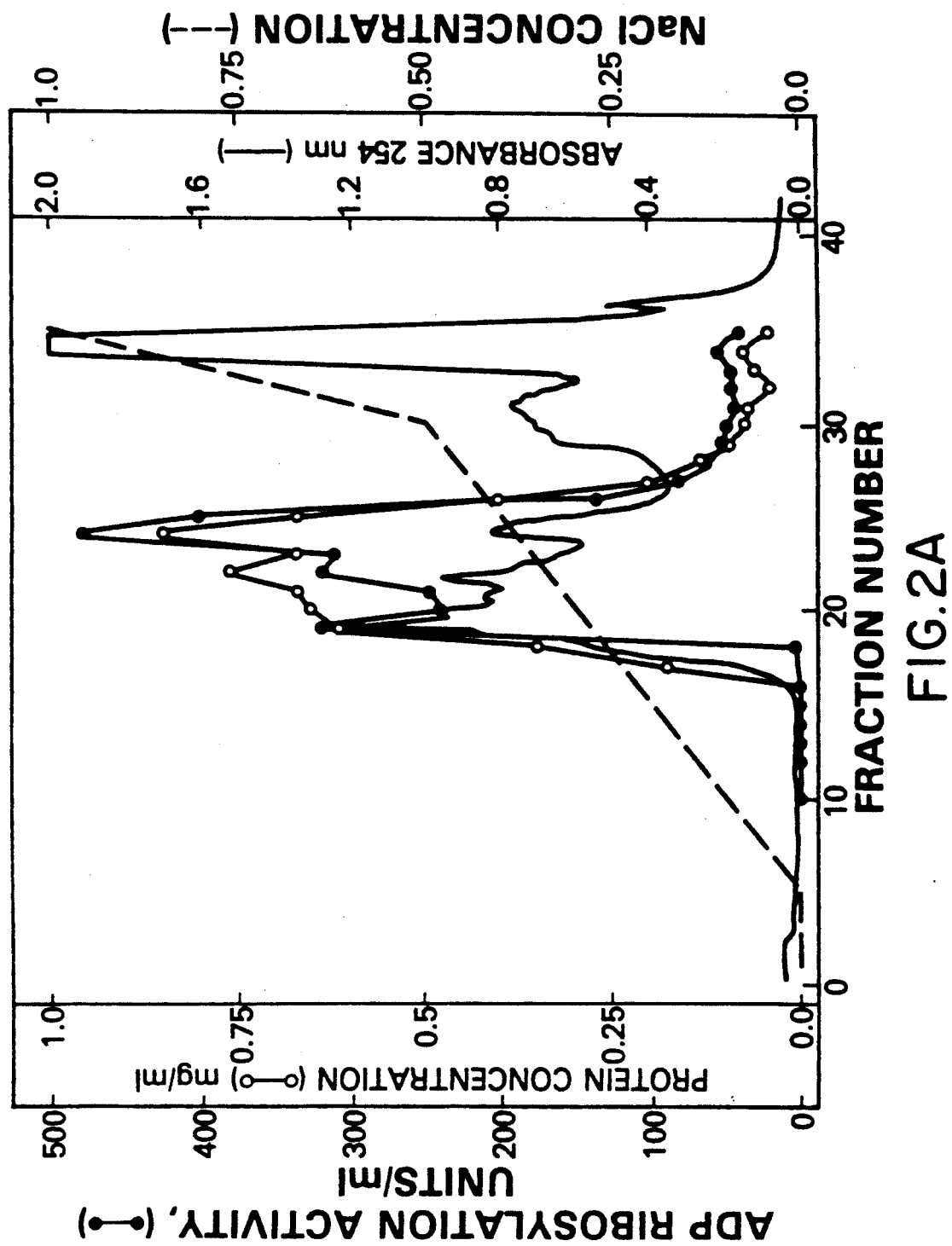
FIG. 2 (parts a and b) shows the results of column chromatography (a) and gel electrophoresis (b) of the CD4(178)-PE40.
Figure 2B:
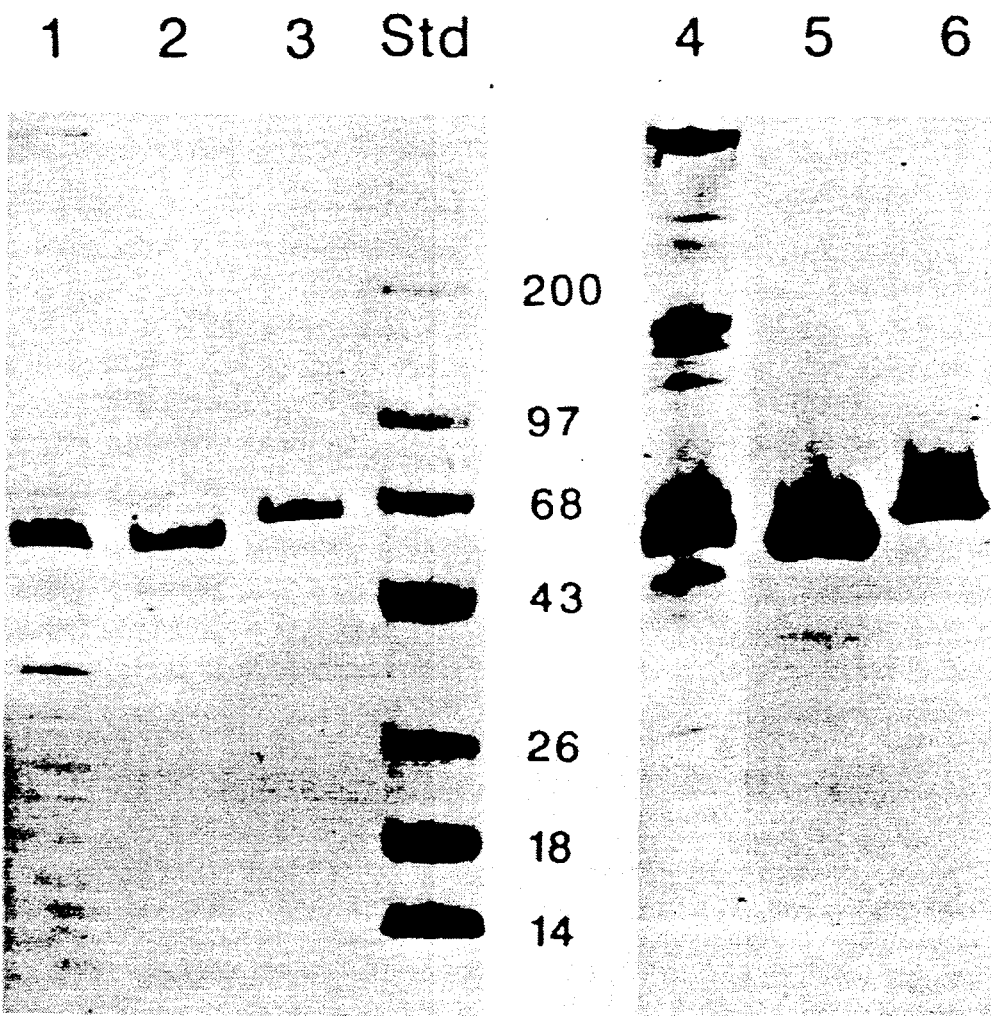

A highly purified monomeric form of CD4(178)-PE40 was obtained by chromatography of the renatured protein on a mono Q column (FIG. 2a). Analysis of each fraction by polyacrylamide gel electrophoresis in the presence of sodium dodecyl sulfate (SDS) indicated that fraction 19 contained at least 80% pure monomeric fusion protein that reacted with a rabbit polyclonal antibody to PE (FIG. 2). Further purification of fraction 19 on a TSK-250 gel filtration column showed that the fusion protein eluted as a symmetrical peak at the elution volume expected for a 60,000 Mr protein. SDS polyacrylamide gel electrophoresis revealed the presence of a single band corresponding to a protein of about 60,000 Daltons.

To determine the ability of CD4(178)-PE40 to bind gp120, two types of assays were performed (FIG. 3). First, CD4(178)-PE40 was mixed with soluble [$^{35}$S]methionine-labeled gp120, and the immune complexes obtained with anti-PE serum were bound to protein A agarose and resolved by SDS polyacrylamide gel electrophoresis. As shown in FIG. 3a, labeled gp120 was specifically co-precipitated along with CD4(178)-PE40. Second, the binding of CD4(178)-PE40 to cell-associated gp120 was established by immunofluorescence microscopy. The HIV envelope gylcoprotein was produced in CV-1 cells using a vaccinia based expression system. Both the external gp120 and transmembrane gp41 subunits are present on the surface of cells infected with a recombinant vaccinia virus encoding gp 160; furthermore, such cells form extensive syncytia when mixed with CD4-bearing human cells. FIG. 3b shows that CD4(178)-PE40 bound to CV-1 cells that had been infected with a recombinant vaccinia virus encoding gp160 but not to cells infected with a control recombinant vaccinia virus. Additional specificity controls indicated that the fluorescence was not observed if either the CD4(178)-PE40 or the anti-PE antibodies were omitted. Taken together, these results demonstrate that CD4(178)-PE40 binds to gp120 in solution or on the cell surface.

Binding of authentic PE to cells followed by internalization and translocation to the cytoplasm results in ADP-ribosylation of elongation factor 2 and the consequent inhibition of protein synthesis and cell death. Two assay systems were employed to determine whether CD4(178)-PE40 is selectively internalized and translocated by cells expressing the HIV envelope glycoprotein, leading to inhibition of protein synthesis. First, the effects on cells infected with recombinant vaccinia viruses were examined. FIG. 4a shows that protein synthesis in CV-1 cells infected with a recombinant vaccinia virus encoding gp160 was severely inhibited after only 4 hours of exposure to CD4(178)-PE40 (ID$_{50}$ of 27 ng/ml). By contrast, cells infected with a control recombinant vaccinia virus were much less sensitive to the hybrid toxin (ID$_{50}$>1,000 ng/ml). When authentic PE was employed, cells infected with the gp160-expressing and the control recombinant vaccinia viruses were equally sensitive (ID$_{50}$=100 ng/ml); they were also equally insensitive to PE40, which lacks a cell binding domain (ID$_{50}$>1,000 ng/ml). We conclude that expression of the HIV envelope protein rendered cells very sensitive to the hybrid toxin and that the specificity was conferred by the CD4 moiety.

As a second system to evaluate the selectivity and effectiveness of CD4(178)-PE40, an uninfected human lymphocyte cell line (A3.01) and a daughter cell line (8E5) that is chronically infected with HIV were tested as targets. The 8E5 cells are especially suitable for experimental studies since they contain a single integrated viral genome, constitutively synthesize HIV proteins including gp120, form syncytia when mixed with CD4-bearing cells, and produce budding particles. Addition of CD4(178)-PE40 to 8E5 cells led to inhibition of protein synthesis: the ID$_{50}$ of 100 ng/ml (determined at 17.5 hours after addition of toxin) indicated that the HIV-infected cells were highly sensitive to the hybrid toxin (FIG. 4b). By contrast, protein synthesis in the parental A3.01 cells was resistant to CD4(178)-PE40 under these conditions. Both cell lines were moderately sensitive to authentic PE (ID$_{50}$=500 ng/ml) and unaffected by PE40.

In evaluating the therapeutic potential of a hybrid toxin, effects on cells other than the desired targets must be considered. Since the natural receptor for CD4 is believed to be the class II major histocompatibility (MHC) molecules on the surface of antigen-presenting cells, B-lymphocytes and macrophages might be affected by the chimeric toxin. Tests indicated, however, that CD4(178)-PE40 did not inhibit protein synthesis in Raji cells, a B-cell line which expresses large amounts of MHC class II molecules. This result is consistent with a published report that soluble CD4 has no inhibitory effect on CD4/MHC class II interactions in vitro, and suggests that monomeric forms of CD4 may have relatively weak affinity for class II antigens.

These results demonstrate that HIV-infected lymphocytes were selectively killed by a hybrid toxin made in E. coli containing a 178 amino acid segment of human CD4 linked to the second and third domains of the potent Pseudomonas exotoxin A. Additional experiments with recombinant vaccinia virus expression vectors indicated that the sensitivity to the chimeric toxin resulted from expression of the HIV envelope protein. For both the HIV-infected and the recombinant vaccinia virus-infected cell systems, selectively was mediated by the CD4 moiety of the chimeric protein. The concentrations of purified renatured CD4(178)-PE40 required for 50% inhibition of protein synthesis in these experiments ranged from 27 to 100 ng per ml. Based on data with other PE fusion proteins, it is not difficult to attain such levels in animals without significant nonspecific toxicity. Furthermore, CD4(178)-PE40 could be useful against cells infected with diverse strains of HIV-1 as well as HIV-2, since the envelope proteins of all these viruses retain binding specificity for CD4 despite extensive antigenic variation.

In summary, the data presented herein clearly establish that a fusion protein CD4(178)-PE40 specifically and efficiently kills HIV-infected cells. This allows the use of this recombinant toxin as a therapeutic agent for the control and treatment of AIDS. A therapeutic composition in accordance with the present invention comprises an effective amount of the recombinant toxin to kill HIV-infected cells in a pharmaceutically acceptable vehicle, if necessary, such as physiological saline, buffered solutions and the like. The toxin may be administered by any suitable route, systemically or locally as deemed more effective. The method of controlling or treating AIDS comprises contacting HIV-infected cells with the effective amount of the recombinant toxin [CD4(178)-PE40 fusion protein] to kill HIV-infected cells or inhibit fusion and syncytia formation resulting subsequent to HIV-infection.

It may be important to note here that the present invention differs significantly from and has advantages over other treatment modalities of AIDS at least in the following respects.

I. It has been reported that soluble derivatives of CD4 block HIV infectivity of cells in culture, presumably by competing for the ability of the virus to bind to cell-associated CD4. Without being bound to any specific theory, it is postulated that the invention described herein acts by a different mechanism, namely by killing cells which have already been infected with HIV. In this regard, it has been reported that soluble CD4 is much less effective when added after the virus has been allowed to infect the cell, unlike the CD4-toxin which kills cells after infection has occurred. It should be noted that the hybrid toxin may also produce competitive inhibition of infectivity seen with soluble CD4 in addition to its targeted killing of HIV-infected cells.

II. Selective killing of HIV-infected cells using an immunotoxin composed of an anti-gp120 mouse monoclonal antibody chemically conjugated to protein toxin (ricin) has also been reported. However, the CD4(178)-PE40 fusion protein of the present invention possesses numerous advantages over this immunotoxin: (a) In the case of the immunotoxin the antibody used is type specific, and does not bind to gp120 from diverse isolates of HIV-1. In contrast, CD4(178)-PE40 may be used against divergent strains of HIV-1 as well as against HIV-2, since all these viruses use CD4 as the receptor. Because of this requirement for CD4 receptor specificity, it is extremely unlikely that variants of HIV, resistant to CD4-toxin hybrid proteins, will arise, whereas variants which no longer bind type-specific monoclonal antibodies often arise. (b) The immunotoxin is produced by chemical coupling procedures which are difficult to control, thereby compromising the uniformity of the conjugate and also result in low yield. In contrast, the recombinant CD4(178)-PE40 fusion protein can be produced in large quantities in a bacterial expression system using standard procedures. (c) The mouse immunoglobulin component of the immunotoxin is likely to be immunogenic in human subjects, thereby compromising its effectiveness. In contrast, with CD4-toxin fusion proteins, the targeting to gp120-expressing cells is achieved by a fragment of human CD4, which is likely to be less immunogenic in humans.

III. Selective killing of HIV-infected cells in vitro by liposomes containing diphtheria toxin fragment A has also been reported. Clearly, this is quite distinct from the fusion-protein methodology of the present invention.

Having described certain aspects of the present invention, various modifications thereof which can be achieved by one of ordinary skill in the art, are now listed.

A. Variations in the CD4 portion. This can be achieved, for example, by differences in length of the CD4 sequence. Shorter or longer versions of the CD4 sequence can be found which can also be attached to toxins to achieve selective killing of HIV-infected cells. The length of the CD4 sequence can have important consequences for the affinity for gp120, for the relative affinities for gp120 vs. class II antigens, for the physical accessibility to different regions within the body, and for the immunogenicity. In addition, site-specific mutagenesis can be used to decrease the affinity of CD4 for normal cellular antigens, and/or increase the affinity for gp120. Such mutations would widen the window between effective therapeutic dosages and unwanted toxic side effects.

B. Variation in the toxin portion. Modifications of PE can be made. By selective mutagenesis or deletion, the immunogenicity of the PE sequence can be reduced and the potency of the hybrid toxin increased (e.g., by enhancing translocation or catalytic activity).

In addition to PE, other toxins such as ricin and diphtheria toxin fragment A could be similarly employed in context of fusion technique described herein.

C. Expression systems

Bacterial. By employing, for example, certain *E. coli* expression system, secreted forms of the hybrid toxin can be made obviating the need for denaturation/renaturation.

Eukaryotic. Mammalian, vaccinia virus, baculovirus, and yeast expression systems can also be used as advantageous expression systems as is well known to one of ordinary skill in the art.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A chimeric gene which encodes a hybrid protein, wherein the hybrid protein comprises a sequence of human CD4 containing a binding site for HIV gp120 linked to a sequence of Pseudomonas exotoxin A essential for cell toxicity.

2. The chimeric gene of claim 1, wherein the cytotoxic protein includes sequences of Pseudomonas exotoxin A essential for cell toxicity.

3. The gene of claim 2 encoding CD4(178)-PE40 hybrid protein.

4. The gene of claim 3 inserted in a cloning vector.

5. The gene of claim 4 wherein said cloning vector has all the functional characteristics of ATCC deposit No. 67739.

6. The gene of claim 5 expressed in *E. coli.*

7. The chimeric gene of claim 1, wherein the sequence of human CD4 includes residues 1-178.

8. The chimeric gene of claim 7, wherein the cytotoxic protein includes sequences of Pseudomonas exotoxin A essential for cell toxicity.

9. The chimeric gene of claim 1, wherein the cytotoxic protein is PE40.

* * * * *